United States Patent [19]

Broecker et al.

[11] 4,192,807

[45] Mar. 11, 1980

[54] MANUFACTURE OF γ-BUTYROLACTONE FROM MALEIC ANHYDRIDE

[75] Inventors: Franz J. Broecker, Ludwigshafen; Gerd Duembgen, Dannstadt-Schauernheim; Helmut Glietenberg; Ernest Miesen, both of Ludwigshafen; Matthias Schwarzmann, Limburgerhof, all of Fed. Rep. of Germany

[73] Assignee: BASF Aktiengesellschaft, Fed. Rep. of Germany

[21] Appl. No.: 834,780

[22] Filed: Sep. 19, 1977

[30] Foreign Application Priority Data

Sep. 22, 1976 [DE] Fed. Rep. of Germany ....... 2642533

[51] Int. Cl.² ............................................ C07D 307/32
[52] U.S. Cl. ................................................. 260/343.6
[58] Field of Search ....................................... 260/343.6

[56] References Cited

U.S. PATENT DOCUMENTS

| 3,113,138 | 12/1963 | Borivoj | 260/343.6 |
|---|---|---|---|
| 3,580,930 | 5/1971 | Miya | 260/343.6 |
| 3,890,361 | 6/1975 | Kanetaka | 260/343.6 |
| 3,948,805 | 4/1976 | Michalczyk et al. | 260/343.6 |
| 3,994,928 | 11/1976 | Michalczyk et al. | 260/343.6 |
| 4,001,282 | 1/1977 | Miller | 260/343.6 |
| 4,006,165 | 2/1977 | Michalczyk et al. | 260/343.6 |
| 4,025,534 | 5/1977 | Sandhack | 260/343.6 |

OTHER PUBLICATIONS

Kirk–Othmer Encyclopedia of Chemical Technology, vol. 7, p. 204.

*Primary Examiner*—Natalie Trousof
*Assistant Examiner*—Jane T. Fan
*Attorney, Agent, or Firm*—Keil & Witherspoon

[57] ABSTRACT

γ-Butyrolactone is manufactured by hydrogenating maleic anhydride in the presence of butyrolactone as the solvent. The hydrogenated reaction mixture, which contains butyrolactone, succinic anhydride and succinic acid, is fractionated in a thin film evaporator.

5 Claims, 1 Drawing Figure

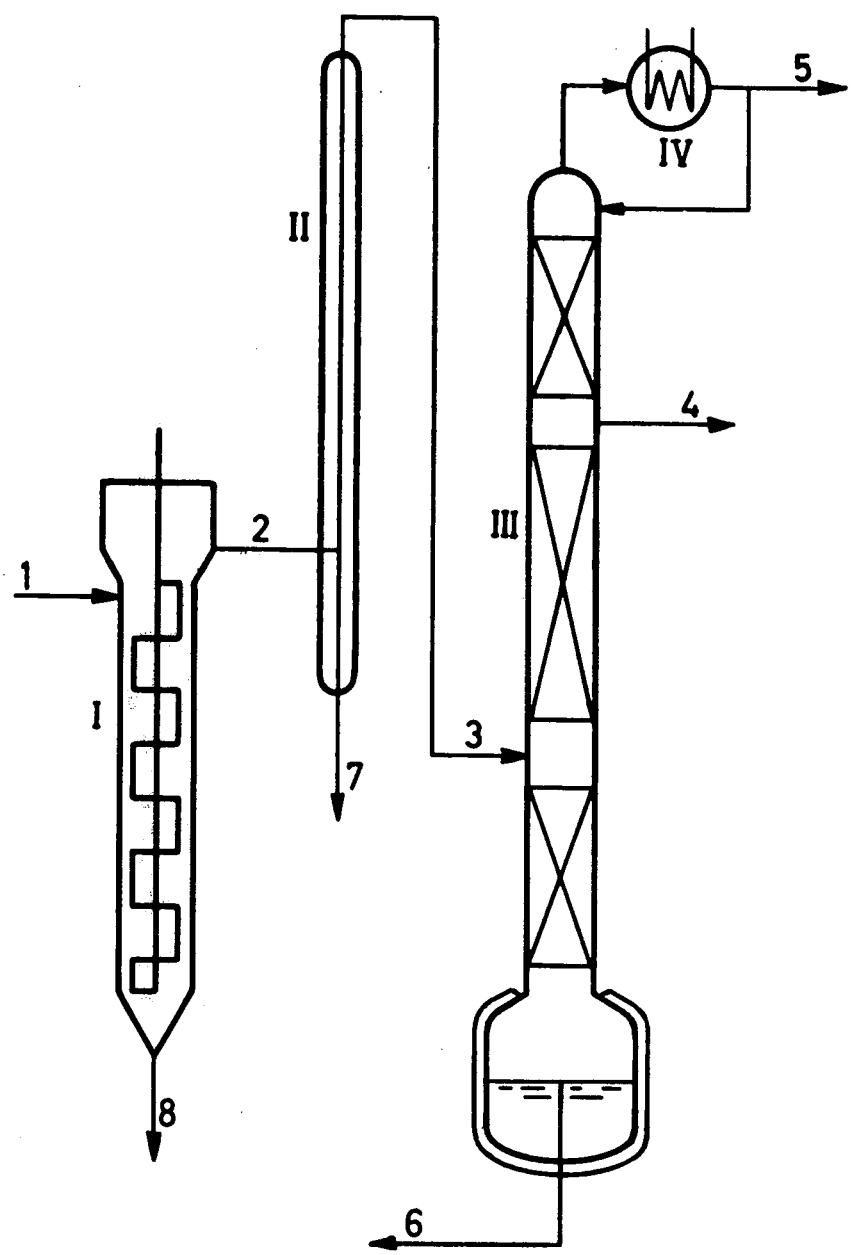

MANUFACTURE OF γ-BUTYROLACTONE FROM MALEIC ANHYDRIDE

The present invention relates to a process, which can be carried out continuously, for the manufacture of γ-butyrolactone (BTL) by hydrogenating maleic anhydride (MA) in the presence of butyrolactone as the solvent, in which the hydrogenated reaction mixture, which contains butyrolactone, succinic anhydride (SA) and succinic acid (SAC) is fractionated in a thin film evaporator.

It has been disclosed that in the conventional hydrogenation of maleic anhydride at above 230° C. and up to 250° C. (whether the product is succinic anhydride or butyrolactone), high molecular weight pitch-like by-products are formed, because maleic anhydride and the secondary products formed during the hydrogenation readily undergo condensation reactions and polymerization reactions; the amount of these by-products increases with the hydrogenation temperature so that it would be advantageous to carry out the catalytic hydrogenation at as low a temperature as possible.

However, if maleic anhydride is hydrogenated—either directly or with intermediate isolation of succinic anhydride—at a particularly low temperature (in the range from 70° to 210° C.) to give butyrolactone, the water formed during the hydrogenation inevitably reacts with excess succinic anhydride to give succinic acid, which can no longer be hydrogenated; the acid has to be decomposed to give succinic anhydride and water and the anhydride then recycled to the hydrogenation process.

On the other hand, even if the process is carried out under mild conditions, side-reactions occur. As a result, if the hydrogenation is carried out continuously—which necessitates the recycling of part-streams of the product—over fixed bed catalysts, a deposit of by-products which reduces the activity of the catalyst is observed sooner or later. For this reason, only suspension processes have hitherto been used industrially for the manufacture of butyrolactone for maleic anhydride, and such processes generally present difficulties if they are carried out continuously.

It is an object of the present invention to avoid the by-products of the hydrogenation or the consequences of these, and to render reversible, in a technologically acceptable and economical manner, the hydration of succinic anhydride, which occurs as a side-reaction.

We have found that this object is achieved and that butyrolactone is obtained in an advantageous manner by hydrogenation of maleic anhydride, in which reaction water is formed together with the by-products succinic anhydride and succinic acid, if maleic anhydride and recycled or unconverted succinic anhydride are hydrogenated, preferably continuously, at below 210° C., the hydrogenated reaction mixture is fed as a liquid into the upper part of a thin film evaporator at not less than 235° C., products of low volatility are separated off as a liquid and the products in vapor form are partially condensed, succinic anhydride being separated off and recycled, and are then fractionally distilled in the conventional manner, butyrolactone being isolated.

Accordingly, the invention broadly comprises decomposing the succinic acid formed and removing high-boiling by-products conjointly in a thin film evaporator, e.g. a falling film (Sambay) evaporator.

In this process, succinic anhydride is separated from the stream of vapor by partial condensation and is recycled to the hydrogenation process. Butyrolactone and water are separated in a subsequent distillation and the former is isolated in the pure form. The essential advantage of this process is that high-boiling by-products formed during the hydrogenation can be removed continuously. This ensures a long life of the hydrogenation catalysts.

The resulting process is schematically illustrated in the accompanying drawing. The hydrogenation product, which contains butyrolactone, succinic acid, succinic anhydride and by-products, passes via (1) into the evaporator (I). High-boiling by-products are removed at (8) whilst the vapors leave the evaporator at (2). The temperature and, where relevant, the residence time must be so chosen in relation to the dimensions of the evaporator that the succinic acid is substantially decomposed into succinic anhydride and water. For this, evaporator temperatures of from 235° to 350° C., preferably from 260° to 300° C., are chosen. With conventional constructions, the residence time may be from 0.25 to 2.5 minutes; in general, it must be determined by a suitable experiment. The vapor mixture containing butyrolactone, succinic anhydride, water and succinic acid now passes into the partial condenser (II). There succinic anhydride, some of the butyrolactone and any non-decomposed succinic acid are condensed, using a relatively short residence time, at from 150° to 250° C., preferably from 170° to 220° C. The condensate leaves the condenser at (7) and is recycled to the hydrogenation stage. The vapor mixture at the top of the condenser consists of butyrolactone, water and small amounts of succinic anhydride and/or succinic acid. This gas mixture passes, at (3), into the distillation unit (III) where it is fractionated, so that pure butyrolactone is obtained at (4) whilst at the top of the column water is continuously discharged at (5). Small amounts of succinic anhydride, succinic acid and butyrolactone which may still be found at the bottom of the column can be recycled to the hydrogenation stage via (6).

EXAMPLE 1

(compare Figure)

A liquid product stream (1) of 1 kg/h, coming from the hydrogenation stage of a continuously operated installation, is composed of 73.8% by weight of BTL, 15.1% by weight of SAC, 10.9% by weight of SA and 0.2% by weight of high-boiling constituents. It is fed to a Sambay evaporator which is kept at 260° C. and run at a rotor speed of 750 rpm. The condenser is a jacketed tube at a temperature of 200° C. The high-boiling by-products are removed at (8) and discarded. 0.474 kg/h of a liquid composed of 52.8% by weight of BTL, 38.14% by weight of SA and 9.06% by weight of SAC are separated out from the vapor mixture in the condenser (II) and recycled to the hydrogenation stage via (7). 0.524 kg/h of vapors are fed to the distillation unit via (3). The composition of the vapor mixture is 92.09% by weight of BTL, 4.03% by weight of SA, 0.06% by weight of SAC and 3.28% by weight of $H_2O$. At the top of the column, water containing about 1% by weight of BTL is obtained while at (4) virtually the entire BTL, containing less than 0.5% by weight of water, is obtained and at the bottom of the column SA, SAC and BTL, which are recycled to the hydrogenation, are collected.

EXAMPLE 2

The hydrogenation product is composed of 73.5% by weight of BTL, 15.2% by weight of SAC, 10.7% by weight of SA and 0.6% by weight of high-boiling by-products. The evaporator is kept at 280° C. and in other respects the procedure described above is followed. The partial condenser is kept at 210° C. Here, 0.329 kg/h of a liquid composed of 51.7% by weight of BTL, 36.9% by weight of SA and 11.4% by weight of SAC are separated out and pumped back to the hydrogenation stage. 0.665 kg/h of a vapor mixture composed of 84.25% by weight of BTL, 11.71% by weight of SA, 1.04% by weight of SAC and 3% by weight of $H_2O$ are passed to the distillation unit. Water containing about 1% by weight of BTL, and BTL containing less than 0.5% by weight of water are recovered. The material at the bottom of the distillation column is recycled to the hydrogenation stage.

We claim:
1. In a process for the manufacture of butyrolactone by hydrogenating maleic anhydride in which water and, as by-products, succinic anhydride and succinic acid are formed, the improvement which comprises:
   (a) continuously maleic anhydride and recycled or unconverted succinic anhydride over a fixed catalyst bed at a temperature below 210° C.,
   (b) feeding the hydrogenated reaction mixture as a liquid into the upper part of a thin film evaporator at a temperature of not less than 235° C., wherein succinic acid is substantially decomposed to succinic anhydride and water, and a liquid phase containing products of low volatility and a vapor phase containing butyrolactone, succinic anhydride, water and any undecomposed succinic acid are formed,
   (c) separating the products of low volatility as a liquid,
   (d) conducting the vapor phase to a condensing means,
   (e) partially condensing the vapor phase, wherein succinic anhydride and unconverted succinic acid are separated and recycled,
   (f) conducting the non-condensed portion of the vapor phase from step (e) to a distillating means, and
   (g) fractionally distilling said non-condensed portion and isolating the butyrolactone.

2. A process as set forth in claim 1, which is operated continuously.

3. A process as set forth in claim 1, in which the hydrogenation is carried out at from 70° to 210° C.

4. A process as set forth in claim 1, in which the thin film evaporator is kept at from 260° to 300° C.

5. A process as set forth in claim 1, in which the residence time of the reaction mixture in the thin film evaporator is from 0.25 to 2.5 minutes.

* * * * *